United States Patent
Yamada

(10) Patent No.: US 8,088,142 B2
(45) Date of Patent: *Jan. 3, 2012

(54) SINUS MEMBRANE PERFORATION PATCHING MATERIAL CARRYING INSTRUMENT

(76) Inventor: Jason M. Yamada, Rolling Hills Estates, CA (US)

(*) Notice: Subject to any disclaimer, the term of this patent is extended or adjusted under 35 U.S.C. 154(b) by 1092 days.

This patent is subject to a terminal disclaimer.

(21) Appl. No.: 11/895,814

(22) Filed: Aug. 28, 2007

(65) Prior Publication Data

US 2008/0161835 A1     Jul. 3, 2008

Related U.S. Application Data

(60) Provisional application No. 60/882,940, filed on Dec. 31, 2006.

(51) Int. Cl.
*A61B 17/50* (2006.01)

(52) U.S. Cl. .................................... 606/210

(58) Field of Classification Search ............ 132/73.5, 132/75.3; 433/3–4, 159; 606/205–210, 131–133; D24/143; D8/52, 54
See application file for complete search history.

(56) References Cited

U.S. PATENT DOCUMENTS

| | | | | |
|---|---|---|---|---|
| 2,214,984 A * | 9/1940 | Bachmann | ............ | 606/210 |
| 3,392,727 A * | 7/1968 | Hanlon | ............ | 606/210 |
| 4,001,940 A * | 1/1977 | Cusato | ............ | 433/3 |
| 4,559,853 A * | 12/1985 | Oye | ............ | 81/420 |
| 4,950,281 A * | 8/1990 | Kirsch et al. | ............ | 606/207 |
| 4,955,896 A * | 9/1990 | Freeman | ............ | 606/210 |
| 5,019,091 A * | 5/1991 | Porat et al. | ............ | 606/205 |
| 5,147,369 A * | 9/1992 | Wagner | ............ | 606/107 |
| 5,520,704 A * | 5/1996 | Castro et al. | ............ | 606/208 |
| 5,547,378 A * | 8/1996 | Linkow | ............ | 433/173 |
| 5,711,315 A * | 1/1998 | Jerusalmy | ............ | 128/898 |
| 5,807,016 A * | 9/1998 | Herring et al. | ............ | 403/321 |
| 5,893,307 A * | 4/1999 | Tao | ............ | 81/427 |
| 6,280,459 B1 * | 8/2001 | Doble | ............ | 606/206 |
| 6,517,554 B1 * | 2/2003 | Zhu et al. | ............ | 606/150 |
| 6,776,615 B2 * | 8/2004 | Dietrich | ............ | 433/159 |
| 6,786,719 B2 * | 9/2004 | McGann | ............ | 433/4 |
| 7,621,742 B2 * | 11/2009 | Michaelson | ............ | 433/4 |
| 7,654,997 B2 * | 2/2010 | Makower et al. | ............ | 604/509 |
| 7,837,707 B2 * | 11/2010 | Yamada | ............ | 606/213 |
| 2002/0106609 A1 * | 8/2002 | Palermo et al. | ............ | 433/159 |
| 2002/0127514 A1 * | 9/2002 | Dietrich | ............ | 433/159 |

OTHER PUBLICATIONS

Pikos "Maxillary Sinus Membrane Repair: Update on Technique for Large and Complete Perforations" 2008 Implant Dentistry vol. 17 No. 1 24-31.*
Barone et al "A Clinical Study of the Outcomes and Complications Associated with Maxillary Sinus Augmentation" 2006 The International Journal of Oral and Maxillofacial Implants vol. 21 No. 1 81-85.*
Ardekian et al "The Clinical Significance of Sinus Membrane Perforation During Augmentation of the Maxillary Sinus" 2006 Jornal of Oral Maxillofacial Surgery 64:277-282.*

(Continued)

*Primary Examiner* — Gary Jackson
*Assistant Examiner* — Amy Shipley
(74) *Attorney, Agent, or Firm* — Robert R. Meads

(57) ABSTRACT

A sinus membrane perforation patching material carrying and insertion instrument, comprising a central support for a quantity of a sinus membrane patching material and moveable outer supports spaced laterally outward of the central support for laterally supporting and expanding the patching material as it is forced by the central support upward over the sinus perforation to form a relatively thin laterally extending patch sealed to the sinus membrane and closing and sealing the perforation.

2 Claims, 1 Drawing Sheet

OTHER PUBLICATIONS

Vercellotti "The Piezoelectric Bony Window Osteotomy and Sinus Membrane Elevation: Introduction of a New Technique for Simplification of the Sinus Augmentation Procedure" 2001 The International Journal of Periodontics and Restorative Dentistry vol. 21 No. 6 561-567.*

Proussaefs et al "Effects of Sealing the Perforated Sinus Membrane with a Resorbable Collagen Membrane: A Pilot Study in Humans" 2003 Journal of Oral Implantology vol. XXIX/No. Five 235-241.*

Zijderveld et al "Anatomical and Surgical Findings and Complications in 100 Consecutive Maxillary Sinus Floor Elevation Procedures" 2008 Journal of Oral Maxillofacial Surgery 66: 1426-1438.*

Lundgren et al "Bone Reformation with Sinus Membrane Elevation: A New Surgical Technique for Maxillary Sinus Floor Augmentation" 2004 Clinical Implant Dentistry and Related Research vol. 6 No. 3 p. 1-9.*

* cited by examiner

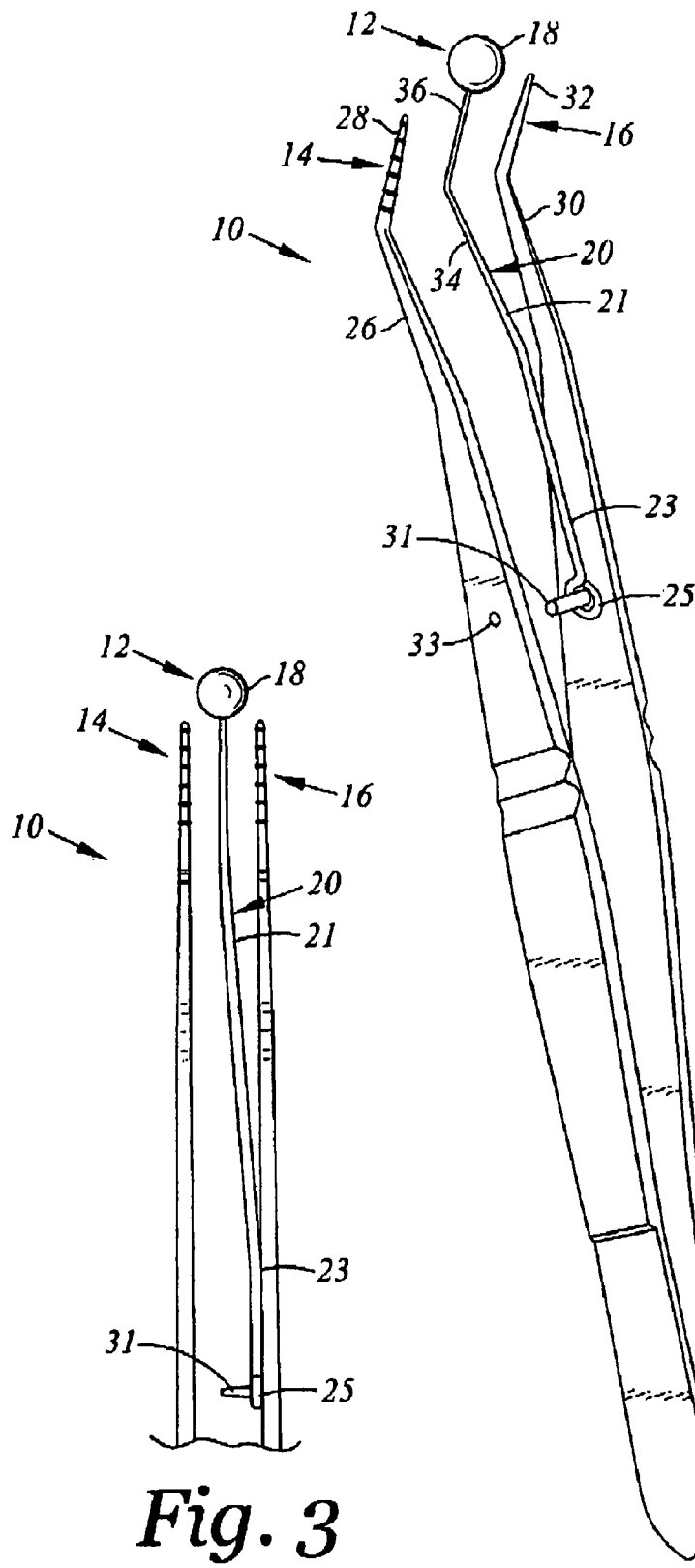
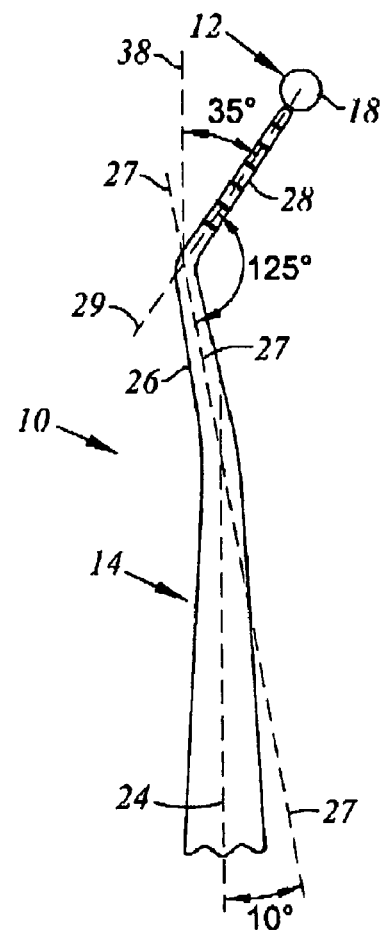
Fig. 1
Fig. 2
Fig. 3

US 8,088,142 B2

SINUS MEMBRANE PERFORATION PATCHING MATERIAL CARRYING INSTRUMENT

RELATED PATENT APPLICATIONS

The present application claims the benefit of U.S. Provisional Patent application Ser. No. 60/882,940 filed Dec. 31, 2006, which is herein incorporated by reference. The present application also relates to the subject matter of the concurrently filed U.S. patent application Ser. No. 11/895,813, entitled "Internal Procedure For Closing Sinus Membrane Perforations", now U.S. Pat. No. 7,837,707 issued Nov. 23, 2010, that is incorporated herein by this reference.

BACKGROUND OF INVENTION

The procedure described in the above-identified concurrently filed United States patent application, is directed to a sinus membrane patching procedure that may be employed if a sinus membrane perforation should occur during a dental procedure or is discovered as having been previously formed during an independent dental procedure or as a result of a physical accident suffered by the patient.

In the membrane patching procedure described in the concurrently filed United Sates patent application, an opening is created in the sinus floor of a patient to expose the portion of the sinus membrane including the perforation. Then, a quantity of a sinus membrane patching material is inserted through the opening to a location adjacent the sinus perforation. Finally, the sinus membrane patching material is laterally expanded and forced against the sinus membrane to seal the perforation.

The present invention is directed to an improved version of an instrument for inserting, laterally expanding and forcing sinus patching material against a sinus membrane to seal a perforation in the sinus membrane.

SUMMARY OF INVENTION

Basically, the instrument of the present invention comprises a central support for a quantity of a sinus membrane patching material and moveable outer supports spaced laterally outward of the central support for laterally supporting and expanding the patching material as it is forced by the central support upward over the sinus perforation to form a relatively thin laterally extending patch sealed to the sinus membrane and closing and sealing the perforation.

BRIEF DESCRIPTION OF ACCOMPANYING DRAWINGS

FIG. 1 is a perspective of the preferred version of the instrument of the present invention.

FIG. 2 is a fragmentary right side view of an upper portion of the instrument of FIG. 1 showing the central support extending upward beyond a right-side one of the outer supports.

FIG. 3 is a fragmentary front view of the upper portion of the instrument shown in FIG. 2 illustrating the connection for the central support to a left-side one of the outer supports and the normal spacing of the outer supports from the central support.

DETAILED DESCRIPTION OF INVENTION

As previously indicated, and as described more fully in the above-referenced concurrently filed United States patent application, in order to seal a sinus perforation according to the method described in that patent application, an opening is created in the sinus floor of a patient exposing a portion of the patient's sinus membrane including the perforation. Next, as shown in FIG. 3 the above-referenced patent application, the actual patching of the sinus perforation may be preceded by a lifting and separation of the perforated sinus membrane from the sinus floor to form a pocket between a lower surface of the sinus membrane and the sinus floor. The patching of the perforation in the sinus membrane is then accomplished as shown in FIGS. 4A and B and FIG. 5 of the above-referenced patent application where an appropriate standard sinus membrane patching material is introduced through the opening into the pocket using a patching material insertion tool designed to carry the material upward into the pocket to a location adjacent and just below the portion of the sinus membrane including the perforation. Basically, as shown in FIG. 4A, during insertion of the sinus membrane patching material through the opening and into the pocket, the outer supports and of the insertion tool are moved laterally against the central support and the patching material is carried by the upper surface of the central support and the upper surfaces of the outer supports. Thus supported, the patching material is moved by the insertion tool upward through the opening and into the pocket to a location adjacent to and immediately below the perforation in the sinus membrane. Then, as shown in FIG. 4B, the insertion tool is moved upwardly until the patching material engages the sinus membrane and extends slightly into the perforation. As this is accomplished, the outer supports are released and moved laterally outward from the central support to aid the central support in laterally extending the patching material to cover the lower surface of the sinus membrane adjacent the perforation and form a patch as shown in FIG. 5 of the above-referenced patent application. In these regards, patching materials useful in the patching of sinus membrane perforations are usually a semi-solid material as initially mounted on the insertion tool as shown in FIG. 4A. However, when the patching material engages the moist surface of the sinus membrane it softens and becomes laterally extendable upon the release of the outer supports and shapeable by the central support to form a sticky adhesive patch covering the perforation and the adjacent lower surfaces of the sinus membrane in response to movement of the central support.

More specifically, relative to the preferred version of the insertion instrument of the present invention and as illustrated in FIG. 1 of the present patent application, the preferred insertion tool or instrument 10 comprises a central support 12 and outer supports 14 and 16 laterally spaced from and laterally moveable relative to the central support 12. The central support may comprise and is illustrated as comprising a ball 18 supported by a vertically extending support rod 20.

As depicted in FIG. 1, the preferred design of the insertion instrument 10 resembles surgical forceps or tweezers having a pair of laterally spaced tongs secured to and extending longitudinally upward from a base for inward lateral movement towards each other when lateral forces are simultaneously applied to the tongs to pinch the free ends of the tongs against each other. In such a preferred design, the outer supports 14 and 16 of the instrument 10 correspond to the pair of tongs of surgical forceps or tweezers, the outer supports being secured and extending longitudinally upward from a base 22 of the instrument 10.

However, the illustrated insertion instrument 10 differs in important structural and function features from such standard surgical forceps or tweezers.

First, among these several structural and function differences, is the central support 12, preferably comprising the ball 18 secured to and supported atop the upper end of the vertically extending support rod 20. As shown in the drawings, the ball 18 extends upward above the upper ends of the outer supports 14 and 16 so that the sinus membrane patching material will drape over the ball and downward onto the outer supports, particularly when the outer supports are moved laterally inward relative to the central support as by an inward pinching of the outer supports.

Second, as shown in FIGS. 1 and 3, at a mid-portion 21, the support rod 20 is bent at an acute angle toward the outer support 16. At a lower portion 23, the support rod 20 is bent to extend generally parallel to an inner surface of the outer support 16. Then, at its lower end 25, the support rod 20 is hook-shaped, looped around and secured (as by welding) to a pin 31 connected to and extending laterally from the outer support 16 to pass through a guide hole 33 in the outer support 14 when the outer supports are pinched together.

Also, among the important structural and functional differences between the insertion instrument 10 and prior surgical forceps and tweezers is the angling of the upper portions of the central and outer supports. As shown in FIGS. 1 and 2, upper end portions 26 and 28 of the outer support 14 and upper end portions 30 and 32 of the outer support 16 and upper end portions 34 and 36 of the support rod 20 are each first bent rearward and upward at the same acute angle relative to a vertical central longitudinal axis 24 of the instrument 10 and then each bent forward and upward at the same acute angle also relative to the axis 24. This is most clearly shown in FIG. 2 where the upper portion 26 of the outer support 14 extending upward from the base connection 22 is bent rearward along an axis 27 at an acute angle of about 10 degrees relative to the instrument axis 24 and then at an upper extension portion 28 is bent forward along an axis 29 at and acute angle of about 35 degrees relative to an axis 38 parallel to the instrument axis 24 or about 125 degrees to the axis 27.

In practice, the above described angling of the central and outer supports aids in the support and lateral extension of the sinus patching material during the application of such material to a sinus membrane and in the forming of the patching material into a relatively thin sealing patch over a perforation in the sinus membrane.

While a particular embodiment of the preferred insertion instrument of the present invention has been illustrated and described above, it is appreciated that changes and modifications may be made in the illustrated embodiment without departing from the spirit of the invention. Accordingly, the scope of present invention is to be limited only by the terms of the following claims.

The invention claimed is:

1. An internal procedure for closing a perforation in a patient's sinus membrane, comprising:
    creating an upward channel in bone leading to a floor of the patient's sinus with an upper open end of the channel exposing a portion of the patient's sinus membrane including the perforation;
    selecting a patching material insertion instrument sized to extend upward into the channel and having an upwardly extending central support surface and upwardly extending outer support surfaces laterally spaced and moveable toward and away from the central support surface;
    moving the outer support surfaces laterally toward the central support surface to a compressed position;
    applying a sinus membrane patching material to the central support surface and to the outer support surfaces in their compressed position;
    inserting the instrument upward into the channel until the patching material on the central and outer support surfaces engages the sinus membrane over the perforation; and
    releasing the outer support surfaces from their compressed position allowing lateral movement and extension of the patching material covering and a sealing of the perforation.

2. The procedure of claim 1 wherein the central support surface of the selected instrument comprises a ball secured to and supported atop an upper end of a vertically extending support rod and the outer support surfaces are secured to and extend longitudinally upward from a base of the instrument on opposite sides of the support rod for lateral movement toward the compressed position and the application of the patching material and lateral movement away from the central support surface during expansion of the patching material and the sealing of the perforation.

* * * * *